United States Patent [19]

Kramer et al.

[11] 4,134,988

[45] Jan. 16, 1979

[54] 2-ACYLOXY-1-PHENOXY-1-IMIDAZOLYL-(1)-3,3-DIMETHYL-BUTANES

[75] Inventors: Wolfgang Krämer; Karl H. Büchel, both of Wuppertal; Wilhelm Brandes, Cologne; Paul-Ernst Frohberger, Leverkusen, all of Germany

[73] Assignee: Bayer Aktiengesellschaft, Leverkusen, Germany

[21] Appl. No.: 763,465

[22] Filed: Jan. 28, 1977

[30] Foreign Application Priority Data

Feb. 7, 1976 [DE] Fed. Rep. of Germany ....... 2604761

[51] Int. Cl.$^2$ .................. A61K 31/415; C07D 233/60
[52] U.S. Cl. ............................... 424/273 R; 260/299; 548/341; 424/245
[58] Field of Search ..................... 548/341; 424/273

[56] References Cited

U.S. PATENT DOCUMENTS

| | | | |
|---|---|---|---|
| 3,796,704 | 3/1974 | Metzger et al. | 548/341 |
| 3,915,984 | 10/1975 | Gebert et al. | 548/341 |
| 3,940,414 | 2/1976 | Krämer et al. | 548/341 |
| 4,005,083 | 1/1977 | Büchel et al. | 260/299 |

OTHER PUBLICATIONS

Buechel et al. I Chem. Abst. 1975, vol. 83, No. 189336a.
Buechel et al. II Chem. Abst. 1976, vol. 84, No. 169551a.
Kraemer et al. I Chem. Abst. 1975, vol. 82, No. 170934t.
Kraemer et al. II Chem. Abst. 1975, vol. 83, No. 179057n.

*Primary Examiner*—Natalie Trousof
*Attorney, Agent, or Firm*—Sprung, Felfe, Horn, Lynch & Kramer

[57] ABSTRACT

2-Acyloxy-1-phenoxy-1-imidazolyl-(1)-3,3-dimethylbutanes of the formula $$\text{(I)}$$

in which
R is alkyl, alkenyl, alkynyl, cycloalkyl, haloalkyl, optionally substituted phenyl or phenoxyalkyl, alkylamino, dialkylamino or optionally substituted phenylamino,
X is halogen, alkyl, cycloalkyl, alkoxy, haloalkyl, alkylthio, alkoxycarbonyl, optionally substituted phenyl or phenoxy, optionally substituted phenylalkyl, amino, cyano or nitro, and
n is 0 or an integer from 1 to 5, or salts or metal salt complexes thereof, which possess fungicidal and bactericidal properties.

10 Claims, No Drawings

2-ACYLOXY-1-PHENOXY-1-IMIDAZOLYL-(1)-3,3-DIMETHYL-BUTANES

The present invention relates to and has for its objects the provision of particular new 2-acyloxy-1-phenoxy-1-imidazolyl-(1)-3,3-dimethyl-butanes and salts and metal salt complexes thereof which possess fungicidal and bactericidal properties, active compositions in the form of mixtures of such compounds with solid and liquid dispersible carrier vehicles, and methods for producing such compounds and for using such compounds in a new way especially for combating pests, e.g. fungi and bacteria, with other and further objects becoming apparent from a study of the within specification and accompanying examples.

It has been disclosed in U.S. Pat. No. 3,682,950 that trityl-1,2,4-triazoles, such as triphenylmethyl-1,2,4-triazole (Compound A), possess a good fungicidal activity. However, their action is not always entirely satisfactory, especially if low amouts and low concentrations are used.

Further, it has been disclosed in U.S. Pat. Nos. 3,898,341 and 3,940,414 that imidazolyl-O,N-acetals, especially 1-imidazolyl-1-phenoxy-3,3-dimethyl-butan-2-ones or -2-ols which are substituted in the phenyl moiety, exhibit good fungicidal properties. However, their activity is also not always entirely satisfactory, especially if low amounts and low concentrations are used. Furthermore, they are not always satisfactorily tolerated by seeds when they are used as a seed dressing.

The present invention provides compounds which are acylated imidazolyl-O,N-acetals or salts or metal salt complexes thereof, the acylated imidazolyl-O,N-acetals being of the general formula

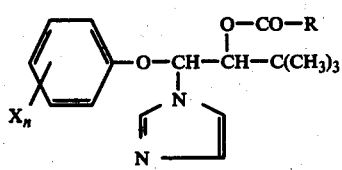

in which
R is alkyl, alkenyl, alkynyl, cycloalkyl, haloalkyl, optionally substituted phenyl or phenoxyalkyl, alkylamino, dialkylamino or optionally substituted phenylamino,
X is halogen, alkyl, cycloalkyl, alkoxy, haloalkyl, alkylthio, alkoxycarbonyl, optionally substituted phenyl or phenoxy, optionally substituted phenylalkyl, amino, cyano or nitro, and
n is 0 or an integer from 1 to 5.

Preferably, R is a straight-chain or branched alkyl with 1 to 8, especially 1 to 6, carbon atoms, straight-chain or branched alkenyl or alkynyl with 2 to 4 carbon atoms, haloalkyl with 1 or 2 carbon atoms and 1 to 5 halogen atoms (especially fluorine or chlorine), cycloalkyl with 5 to 7 carbon atoms, especially cyclohexyl, or R is optionally substituted phenyl, or phenoxyalkyl which is optionally substituted in the phenyl and has 1 or 2 carbon atoms in the alkyl, preferred substituents in the phenyl being halogen, amino, cyano, nitro or alkyl with 1 or 2 carbon atoms, or R is alkylamino or dialkylamino with 1 to 4, especially 1 or 2, carbon atoms in each alkyl or optionally substituted phenylamino with, preferably, halogen, nitro and cyano as substituents; and X is halogen, amino, cyano, nitro, straight-chain or branched alkyl with up to 4 carbon atoms, cycloalkyl with 5 to 7 carbon atoms, especially cyclohexyl, haloalkyl with 1 or 2 carbon atoms and up to 5 halogen atoms (especially fluorine or chlorine); or X is alkoxycarbonyl with a total of up to 5 carbon atoms, or alkoxy or alkylthio each with 1 or 2 carbon atoms; or X is optionally substituted phenyl or phenoxy, preferred possible substituents being halogen, amino, cyano, nitro or alkyl with 1 or 2 carbon atoms; or X is optionally substituted phenylalkyl with 1 or 2 carbon atoms in the alkyl part, in which case alkylcarbonyloxy with a total of up to 3 carbon atoms is the preferred substituent in the alkyl and halogen, nitro and cyano are the preferred substituents, in the phenyl; and n is 0, 1, 2 or 3.

The compounds of the formula (I) possess two asymmetric carbon atoms; they can therefore exist in the erythro-form and in the threo-form. In both cases, they are predominantly in the form of racemates.

Surprisingly, the imidazolyl-O,N-acetals acylated in accordance with the invention exhibit a substantially greater fungicidal activity, especially against species of rust and mildew, than the imidazolyl-O,N-acetals known from the prior art, which are the most closely related active compounds. The active compounds according to the invention thus represent an enrichment of the art.

The invention also provides a process for the production of a compound of the invention in which an imidazolyl derivative of the formula

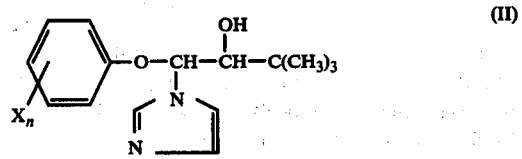

in which
X and n have the abovementioned meanings,
(a) is reacted with an acid halide of the formula

in which
R has the abovementioned meaning and
Hal is halogen, especially chlorine or bromine, in the presence of a solvent, or
(b) is reacted with an acid anhydride of the formula

in which
R has the abovementioned meaning, in the presence of a solvent and optionally in the presence of a catalyst, or
(c) is reacted with a ketene of the formula

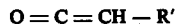

in which
R' is hydrogen, alkyl, alkenyl, alkynyl or halomethyl, in the presence of a solvent and optionally in the presence of a catalyst, or
(d) is reacted with an isocyanate of the formula

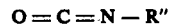

in which
 R″ represents alkyl or optionally substituted phenyl,
in the presence of a solvent and optionally in the presence of a catalyst.

The acylated imidazolyl-O,N-acetals of the formula (I) which are initially obtained in the process, can be converted to salts by reaction with acids, while their metal salt complexes can be obtained by reaction with metal salts. If it is desired that the compounds should be physiologically tolerated by plants or higher animals, then the acids or metal salts will of course be selected accordingly.

If 1-(4-chlorophenoxy)-1-imidazolyl-(1)-3,3-dimethyl-butan-2-ol and acetyl chloride are used as starting materials, the course of the reaction can be represented by the following formula scheme (process variant (a)):

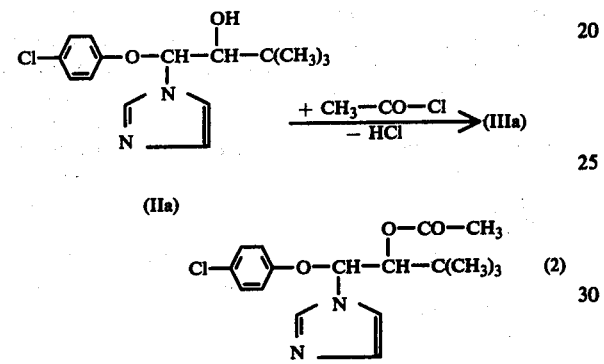

If 1-(4-chlorophenoxy)-1-imidazolyl-(1)-3,3-dimethyl-butan-2-ol and acetic anhydride are used as starting materials, the course of the reaction can be represented by the following formula scheme (process variant (b))

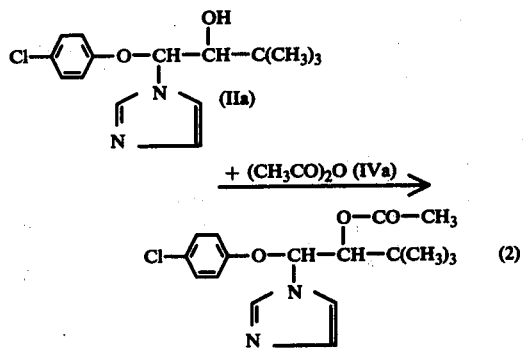

If 1-imidazolyl-(1)-1-phenoxy-3,3-dimethyl-butan-2-ol and methylketene are used as starting materials, the course of the reaction can be represented by the following formula scheme (process variant (c))

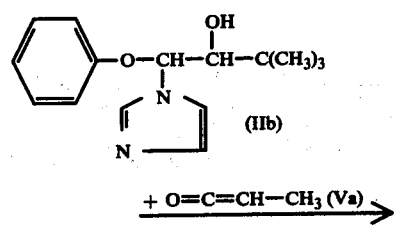

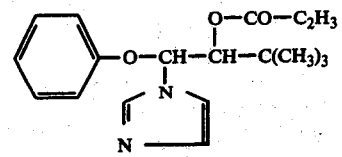

If 1-(2,4-dichlorophenoxy)-1-imidazolyl-(1)-3,3-dimethyl-butan-2-ol and 4-chlorophenyl isocyanate are used as starting materials, the course of the reaction can be represented by the following formula scheme (process variant (d))

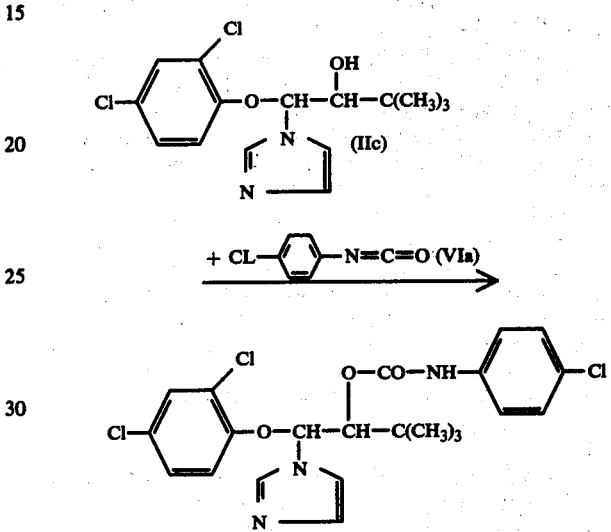

Starting materials of formula (II) are disclosed in U.S. Pat. No. 3,940,414 and can be obtained in accordance with known processes, for example by reducing the ketone derivatives which are formed, by means of aluminum isopropylate or by means of complex hydrides in the presence of a solvent.

Acid halides of formula (III) are known and can be prepared in accordance with customary processes, for example by reacting carboxylic acids or their alkali metal salts with acid halides of phosphorus or sulfur. These methods are known from the general textbooks of organic chemistry.

Acid anhydrides of formula (IV) are known and can be prepared in accordance with generally known processes, for example by treating the alkali metal salts of the carboxylic acids with acid chlorides.

In formula (V) R′ is preferably hydrogen, alkyl with 1 to 7, especially 1 to 5, carbon atoms, alkenyl or alkynyl each with up to 3 carbon atoms or halomethyl with 1 to 3 halogen atoms, especially fluorine or chlorine.

Ketenes of formula (V) are known and can be prepared in accordance with known processes, for example by thermolysis of ketones or by dehydration of carboxylic acids (compare Houben-Weyl, "Methoden der organischen Chemie" ("Methods of Organic Chemistry"), volume 7/4, Georg Thieme Verlag).

In formula (VI) R″ is preferably alkyl with 1 to 4 especially 1 or 2, carbon atoms, or optionally substituted phenyl, the preferred substituents being halogen, nitro and cyano.

Isocyanates of formula (VI) are known and can be prepared in accordance with generally known processes, for example by reaction of amines with phosgene, and subsequent heating.

For some purposes the preferred salts of the compounds of the formula (I) are salts with physiologically tolerated acids. They preferably include the hydrogen halide acids, for example hydrochloric acid and hydrobromic acid, especially hydrochloric acid, phosphoric acid, nitric acid, monofunctional and bifunctional carboxylic acids and hydroxycarboxylic acids, for example acetic acid, maleic acid, succinic acid, fumaric acid, tartaric acid, citric acid, salicylic acid, sorbic acid and lactic acid, and 1,5-naphthalenedisulfonic acid.

The salts of the compounds of the formula (I) can be obtained in a simple manner in accordance with customary methods of forming salts, for example by dissolving the base in ether, for example diethyl ether, and adding the acid, for example nitric acid, and can be isolated in a known manner, for example by filtration, and be purified if appropriate.

Suitable complexes of the compounds of the formula (I) are complexes with metal salts. In this context, metals of main groups II to IV, and of sub-groups I, II and IV to VIII, of the Periodic Table of the Elements, especially copper, zinc, manganese, magnesium, tin, iron and nickel, are often preferred. For many purposes it is preferred that these salts be salts with physiologically tolerated acids. These preferably include the hydrogen halide acids, for example hydrochloric acid and hydrobromic acid, phosphoric acid, nitric acid and sulfuric acid.

The metal salt complexes of the compounds of the formula (I) can be obtained in a simple manner in accordance with customary processes, for example by dissolving the metal salt in an alcohol, for example ethanol, and adding the solution to the base. They can be isolated in a known manner, for example by filtration, and can optionally be purified by recrystallization.

The solvent for the reaction according to process variant (a) is preferably an inert organic solvent. Such solvents preferably include ketones, such as diethyl ketone, and especially acetone and methyl ethyl ketone; nitriles, such as propionitrile and especially acetonitrile; ethers, such as tetrahydrofuran and dioxane; esters, such as ethyl acetate; aromatic hydrocarbons, such as benzene and toluene; and halogenated hydrocarbons, such as methylene chloride, carbon tetrachloride and chloroform.

In carrying out process variant (a), the reaction temperatures can be varied over a substantial range. In general, the reaction is carried out at 0° to 100° C., preferably 20° to 85° C. The reaction is advantageously carried out at the boiling point of the particular solvent.

In carrying out process variant (a), equimolar amounts are preferably used. The compounds of the formula (I) are obtained in the form of their hydrohalides and can be isolated as such, by precipitating them by adding an organic solvent, for example hexane, filtering them off and optionally purifying them by recrystallization. The compounds of the formula (I) can also be isolated in the form of their free base, by adding aqueous sodium bicarbonate solution to the reaction mixture and isolating the base in accordance with customary methods.

Preferred diluents for the reaction according to process variant (b) are the same as for process variant (a). Alternatively, an excess of the particular acid anhydride of the formula (IV) can serve as the solvent.

Catalysts which can be used in process variant (b) are preferably all customary acid and basic catalysts, for example sulfuric acid, hydrochloric acid, hydrobromic acid, boron trifluoride, zinc chloride, sodium acetate, sodium benzoate, sodium carbonate, calcium oxide and magnesium oxide.

In carrying out process variant (b), the reaction temperatures can be varied over a substantial range. In general, the reaction is carried out at 0° to 150° C., preferably 80° to 120° C.

Preferably, equimolar amounts are used in carrying out process variant (b). The compounds of the formula (I) are isolated in the usual manner.

Preferred suitable solvents for the reaction according to process variant (c) are the same as for process variant (a).

Catalysts which can be used in process variant (c) are the same as for process variant (b).

In carrying out process variant (c), the reaction temperatures can be varied over a wide range. In general, the reaction is carried out at −10° to 70° C., preferably 0° to 40° C.

Preferred solvents for the reaction according to process variant (d) are the same as for process variant (a).

Catalysts which can preferably be used in process variant (d) are tertiary bases, such as triethylamine and pyridine, or organo-tin compounds, such as dibutyl-tin dilaurate.

In carrying out process variant (d), the reaction temperatures can be varied over a substantial range. In general, the reaction is carried out at 0° to 100° C., preferably 20° to 40° C.

In carrying out process variant (d), equimolar amounts are preferably used. To isolate the compounds of the formula (I), the solvent may be distilled off and the residue worked up in accordance with customary methods.

The active compounds according to the invention exhibit a powerful fugitoxic action and a bacteriotoxic action. They do not damage crop plants in the concentrations required to combat fungi and bacteria. For these reasons, they are suitable for use as plant protection agents for combating fungi and bacteria. Fungitoxic agents are employed in plant protection for combating Plasmodiophoromycetes, Oomycetes, Chytridiomycetes, Zygomycetes, Ascomycetes, Basidiomycetes and Deuteromycetes.

The active compounds according to the invention have a broad spectrum of action and can be used against parasitic fungi which attack above-ground parts of plants or attack the plants through the soil, and also against seed-borne pathogens.

As already mentioned, the active compounds exhibit a particularly good activity against parasitic fungi on above-ground parts of plants, such as species of Erysiphe and species of Venturia, and also against species of Piricularia and species of Pellicularia. Good effects are achieved against the pathogens of bean rust (*Uromyces phaseoli*) and against fungi which cause powdery mildew diseases, for example the pathogen of powdery mildew of barley (*Erysiphe graminis* var. *hordei*). They furthermore exhibit a high activity against other cereal diseases, such as against powdery mildew of cereals and against cereal rust. The systemic action of the compounds should also be pointed out. Thus, it proves possible to protect plants against fungal attack by supplying the active compound to the above-ground parts of the plant via the soil and the root or via the seed.

As plant protection agents, the compounds according to the invention can be used for the treatment of soil, for the treatment of seed and for the treatment of above-ground parts of plants.

The compounds according to the invention can be well tolerated by plants, can have only a low toxicity to warm-blooded animals and, because of low odour and good toleration by human skin, can be not unpleasant to handle. The toleration by plants and warm-blooded animals depends of course (in the case of compounds in the form of salts or metal complexes) on the respective acids or metals and acids.

The active compounds according to the instant invention can be utilized, if desired, in the form of the usual formulations or compositions with conventional inert (i.e. plant compatible or herbicidally inert) pesticide diluents or extenders, i.e. diluents, carriers or extenders of the type usable in conventional pesticide formulations or compositions, e.g. conventional pesticide dispersible carrier vehicles such as gases, solutions, emulsions, suspensions, emulsifiable concentrates, spray powders, pastes, soluble powders, dusting agents, granules, etc. These are prepared in known manner, for instance by extending the active compounds with conventional pesticide dispersible liquid diluent carriers and/or dispersible solid carriers optionally with the use of carrier vehicle assistants, e.g. conventional pesticide surface-active agents, including emulsifying agents and/or dispersing agents, whereby, for example, in the case where water is used as diluent, organic solvents may be added as auxiliary solvents. The following may be chiefly considered for use as conventional carrier vehicles for this purpose: aerosol propellants which are gaseous at normal temperatures and pressures, such as Freon; inert dispersible liquid diluent carriers, including inert organic solvents, such as aromatic hydrocarbons (e.g. benzene, toluene, xylene, alkyl naphthalenes, etc.), halogenated, especially chlorinated, aromatic hydrocarbons (e.g. chlorobenzenes, etc.), cycloalkanes, (e.g. cyclohexane, etc.), paraffins (e.g. petroleum or mineral oil fractions), chlorinated aliphatic hydrocarbons (e.g. methylene chloride, chloroethylenes, etc.), alcohols (e.g. methanol, ethanol, propanol, butanol, glycol, etc.) as well as ethers and esters thereof (e.g. glycol monomethyl ether, etc.), amines (e.g. ethanolamine, etc.), amides (e.g. dimethyl formamide, etc.), sulfoxides (e.g. dimethyl sulfoxide, etc.), acetonitrile, ketones (e.g. acetone, methyl ethyl ketone, methyl isobutyl ketone, cyclohexanone, etc.), and/or water; as well as inert dispersible finely divided solid carriers, such as ground natural minerals (e.g. kaolins, clays, alumina, silica, chalk, i.e. calcium carbonate, talc, attapulgite, montmorillonite, kieselguhr, etc.) and ground synthetic minerals (e.g. highly dispersed silicic acid, silicates, e.g. alkali silicates, etc.); whereas the following may be chiefly considered for use as conventional carrier vehicle assistants, e.g. surface-active agents, for this purpose: emulsifying agents, such as non-ionic and/or anionic emulsifying agents (e.g. polyethylene oxide esters of fatty acids, polyethylene oxide ethers of fatty alcohols, alkyl sulfates, alkyl sulfonates, aryl sulfonates, albumin hydrolyzates, etc., and especially alkyl arylpolyglycol ethers, magnesium stearate, sodium oleate, etc.); and/or dispersing agents, such as lignin, sulfite waste liquors, methyl cellulose, etc.

Such active compounds may be employed alone or in the form of mixtures with one another and/or with such solid and/or liquid dispersible carrier vehicles and/or with other known compatible active agents, especially plant protection agents, such as other fungicides, bactericides and growth regulating agents, or insecticides, acaricides, nematocides, rodenticides, herbicides, fertilizers, bird repellents, plant nutrients, agents for improving soil structure, etc., if desired, or in the form of particular dosage preparations for specific application made therefrom, such as solutions, emulsions, suspensions, powders, pastes, and granules which are thus ready for use.

As concerns commercially marketed preparations, these generally contemplate carrier composition mixtures in which the active compound is present in an amount substantially between about 0.1–95% by weight, and preferably 0.5–90% by weight, of the mixture, whereas carrier composition mixtures suitable for direct application or field application generally contemplate those in which the active compound is present in an amount substantially between about 0.0001–10%, preferably 0.01–1%, by weight of the mixture. Thus, the present invention contemplates overall compositions which comprise mixtures of a conventional dispersible carrier vehicle such as (1) a dispersible inert finely divided carrier solid, and/or (2) a dispersible carrier liquid such as an inert organic solvent and/or water, preferably including a surface-active effective amount of a carrier vehicle assistant, e.g. a surface-active agent, such as an emulsifying agent and/or a dispersing agent, and an amount of the active compound which is effective for the purpose in question and which is generally between about 0.0001–95%, and preferably 0.01–95%, by weight of the mixture.

The active compounds can also be used in accordance with the well known ultra-low-volume process with good success, i.e. by applying such compound if normally a liquid, or by applying a liquid composition containing the same, via very effective atomizing equipment, in finely divided form, e.g. average particle diameter of from 50–100 microns, or even less, i.e. mist form, for example by airplane crop spraying techniques. Only up to at most about a few liters/hectare are needed, and often amounts only up to about 15 to 1000 g/hectare, preferably 40 to 600 g/hectare, are sufficient. In this process it is possible to use highly concentrated liquid compositions with said liquid carrier vehicles containing from about 20 to about 95% by weight of the active compound or even the 100% active substance alone, e.g. about 20–100% by weight of the active compound.

When the active compounds are used as leaf fungicides, their concentrations in the application forms can be varied within a substantial range. They are, in general, 0.1 to 0.00001 percent by weight, preferably 0.05 to 0.0001 percent.

For the treatment of seed, the amounts of active compound required are generally from 0.001 to 50 g per kilogram of seed, preferably 0.01 to 10 g.

For the treatment of soil, amounts of active compound of 1 to 1,000 g per cubic meter of soil, preferably of 10 to 200 g, are generally required.

In appropriate concentrations, the compounds according to the invention also possess growth-regulating properties.

Furthermore, the present invention contemplates methods of selectively killing, combating or controlling pests, e.g. fungi and bacteria, and more particularly methods of combating fungi, which comprises applying to at least one of correspondingly (a) such fungi, (b) such bacteria, and (c) the corresponding habitat thereof, i.e. the locus to be protected, e.g. to a growing crop, to an area where a crop is to be grown or to a domestic animal, a correspondingly combative or toxic amount, i.e. a fungicidally or bactericidally effective amount, of the particular active compound of the invention alone or together with a carrier vehicle as noted above. The instant formulations or compositions are applied in the usual manner, for instance by spraying, atomizing, vaporizing, scattering, dusting, watering, squirting, sprinkling, pouring, fumigating, dry dressing, moist dressing, wet dressing, slurry dressing, encrusting, and the like.

It will be realized, of course, that the concentration of the particular active compound utilized in admixture with the carrier vehicle will depend upon the intended application. Therefore, in special cases it is possible to go above or below the aforementioned concentration ranges.

The unexpected superiority and outstanding activity of the particular new compounds of the present invention are illustrated, without limitation, by the following examples:

EXAMPLE 1

Powdery mildew of barley (*Erysiphe graminis* var. *Hordei*)/systemic (fungal disease of cereal shoots)

The active compounds were used as pulverulent seed treatment agents. They were prepared by extending the particular active compound with a mixture of equal parts by weight of talc and kieselguhr to give a finely pulverulent mixture of the desired concentration of active compound.

For the treatment of seed, barley seed was shaken with the mixture of active compound and extender in a closed glass bottle. The seed was sown at the rate of 3 × 12 grains in flowerpots, 2 cm deep in a mixture of one part by volume of Fruhstorfer standard soil and one part by volume of quartz sand. The germination and emergence took place under favorable conditions in a greenhouse. 7 days after sowing, when the barley plants had developed their first leaf, they were dusted with fresh spores of *Erysiphe graminis* var. *Hordei* and grown on at 21°–22° C. and 80–90% relative atmospheric humidity and 16 hours' exposure to light. The typical mildew pustules formed on the leaves over the course of 6 days.

The degree of infection was expressed as a percentage of the infection of the untreated control plants. Thus 0% denoted no infection and 100% denoted the same degree of infection as in the case of the untreated control. The more active the compound, the lower was the degree of mildew infection.

The active compounds and concentrations of active compound in the seed treatment agent, as well as the amount used of the latter, and the percentage infection with mildew can be seen from the table which follows:

Table 1

| Powdery mildew of barley test (*Erysiphe Graminis* var. *hordei*)/systemic | | | |
|---|---|---|---|
| Active compounds | Active compound concentration in the dressing in % by weight | Amount of dressing used in g/kg of seed | Infection in % of the untreated control |
| no dressing | — | — | 100.0 |
| $O_2N$—⟨C₆H₄⟩—O—CH(N-imidazolyl)—CO—C(CH₃)₃ (known) (B) | 25 | 10 | 100.0 |
| 2,5-Cl₂—⟨C₆H₃⟩—O—CH(N-imidazolyl)—CO—C(CH₃)₃ (known) (C) | 25 | 10 | 100.0 |
| F—⟨C₆H₄⟩—O—CH(N-imidazolyl)—CH(O—CO—CH₃)—C(CH₃)₃ (3) | 25 | 10 | 25.0 |
| Cl—⟨C₆H₄⟩—O—CH(N-imidazolyl)—CH(O—CO—CH₃)—C(CH₃)₃ | 25 | 10 | 12.5 |

Table 1-continued

Powdery mildew of barley test (*Erysiphe Graminis* var. *hordei*)/systemic

| Active compounds | Active compound concentration in the dressing in % by weight | Amount of dressing used in g/kg of seed | Infection in % of the untreated control |
|---|---|---|---|
| (2) | | | |

EXAMPLE 2

Shoot treatment test/powdery mildew of cereals/-protective (leaf-destructive mycosis)

To produce a suitable preparation of active compound, 0.25 part by weight of active compound was taken up in 25 parts by weight of dimethylformamide and 0.06 part by weight of alkylaryl polyglycol ether emulsifier and 975 parts by weight of water were added. The concentrate was diluted with water to the desired final concentration of the spray liquor.

To test for protective activity, single-leaved young barley plants of the Amsel variety were sprayed with the preparation of active compound until dew-moist. After drying, the young barley plants were dusted with spores of *Erysiphe graminis* var. *hordei*.

After 6 days dwell time of the plants at a temperature of 21°-22° C. and 80-90% atmospheric humidity the occurrence of mildew pustules on the plants was evaluated. The degree of infection was expressed as a percentage of the infection of the untreated control plants. 0% denoted no infection and 100% denoted the same degree of infection as in the case of the untreated control. The more active the compound, the lower was the degree of mildew infection.

The active compounds, active compound concentration in the spray liquor and degrees of infection can be seen from the table which follows:

Table 2

Shoot treatment test/powdery mildew of cereals/protective

| Active compounds | Active compound concentration in the spray liquor in % by weight | Infection in % of the untreated control |
|---|---|---|
| untreated | — | 100.0 |
| 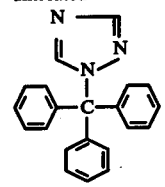 (known) (A) | 0.01 | 100.0 |
| 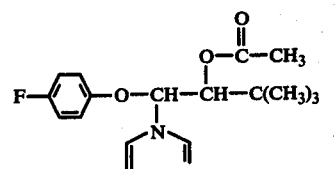 (3) | 0.0005 | 37.5 |
| 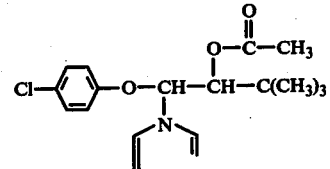 | 0.01 | 3.8 |

Table 2-continued

Shoot treatment test/powdery mildew of cereals/protective

| Active compounds | Active compound concentration in the spray liquor in % by weight | Infection in % of the untreated control |
|---|---|---|
| (2) | | |
| 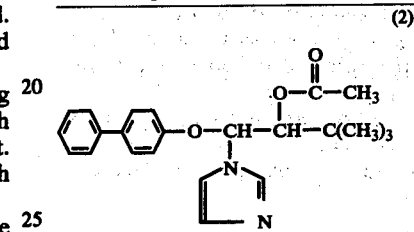 | 0.01 | 12.5 |
| 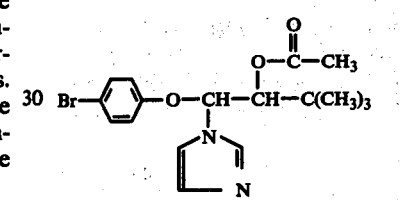 (4) | 0.01 | 0.0 |
| 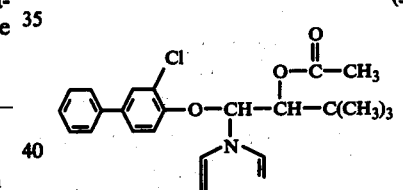 (5) | 0.01 | 25.0 |
| (10) | | |

EXAMPLE 3

Shoot treatment test/cereal rust/protective (leaf-destructive mycosis)

To produce a suitable preparation of active compound, 0.25 part by weight of active compound was taken up in 25 parts by weight of dimethylformamide and 0.06 part by weight of alkylaryl polyglycol ether emulsifier and 975 parts by weight of water were added. The concentrate was diluted with water to the desired final concentration of the spray liquor.

To test the protective activity, one-leaved young wheat plants of the Michigan Amber variety were inoculated with a uredospore suspension of *Puccinia recondita* in 0.1% strength aqueous agar. After the spore suspension had dried on, the wheat plants were sprayed with the preparation of active compound until dew-moist and were placed, for incubation, in a greenhouse for 24 hours at about 20° C. and 100% relative atmospheric humidity.

After 10 days dwell time of the plants at a temperature of 20° C. and 80-90% atmospheric humidity, the occurrence of rust pustules on the plant was evaluated. The degree of infection was expressed as a percentage of the infection of the untreated control plants. 0% denoted no infection and 100% denoted the same degree of infection as in the case of the untreated control. The active compound was the more active, the lower was the degree of rust infection.

The active compounds, active compound concentrations in the spray liquor and degree of infection can be seen from the table which follows:

Table 3

| Shoot treatment test/cereal rust/protective | | |
|---|---|---|
| Active compounds | Active compound concentration in the spray liquor in % by weight | Infection in % of the untreated control |
| untreated | — | 100.0 |
| 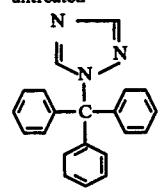 (known) (A) | 0.025 | 100.0 |
| 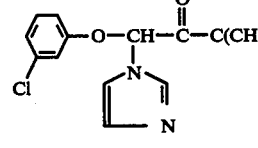 (known) (D) | 0.025 | 100.0 |
| 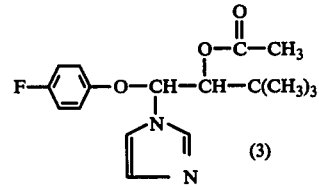 (3) | 0.025 | 0.0 |
| 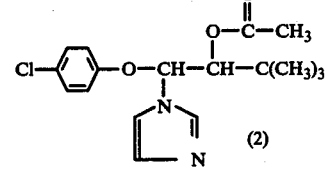 (2) | 0.025 | 28.8 |
| 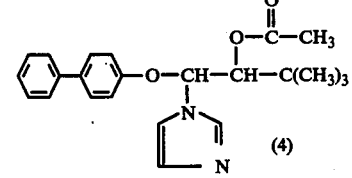 (4) | 0.025 | 40.0 |
| 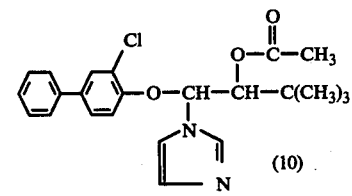 (10) | 0.025 | 70.0 |

Table 3-continued

| Shoot treatment test/cereal rust/protective | | |
|---|---|---|
| Active compounds | Active compound concentration in the spray liquor in % by weight | Infection in % of the untreated control |
| 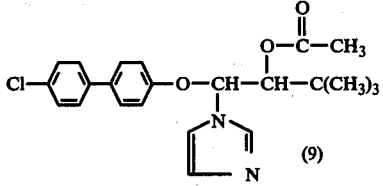 (9) | 0.025 | 12.5 |
| 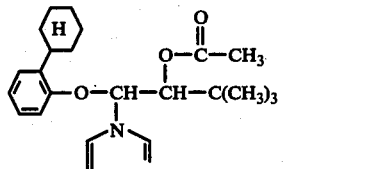 (8) | 0.025 | 75.0 |
| 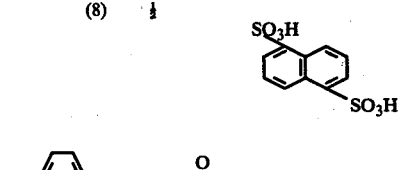 (7) | 0.025 | 66.3 |
| 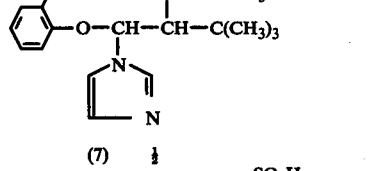 (6) | 0.025 | 66.3 |

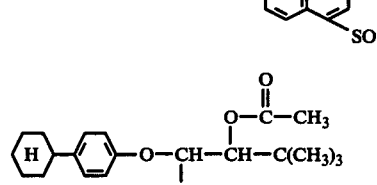
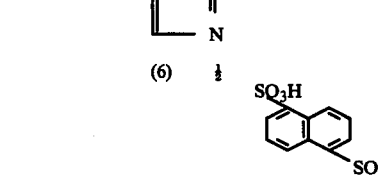

EXAMPLE 4

*Uromyces* test (bean rust)/protective
Solvent: 4.7 parts by weight of acetone
Emulsifier: 0.3 part by weight of alkylaryl polyglycol ether
Water: 95 parts by weight The amount of active compound required for the desired concentration of active compound in the spray liquor was mixed with the stated amount of the solvent and the concentrate was diluted with the stated amount of water which contained the stated additives.

The young bean plants, which were in the 2-leafed stage, were sprayed with the spray liquor until dripping wet. The plants remained in a greenhouse for 24 hours at 20°-22° C. and a relative atmospheric humidity of 70% in order to dry. They were then inoculated with an aqueous uredospore suspension of the causative organism of bean rust (*Uromyces phaseoli*) and incubated for 24 hours in a dark humidity chamber at 20°-22° C. and 100% relative atmospheric humidity.

The plants were then set up in a greenhouse under intensive illumination for 9 days at 20°-22° C. and a relative atmospheric humidity of 70-80%.

10 days after the inoculation, the infection of the plants was determined. The ratings obtained were converted to % infection. 0% denoted no infection and 100% denoted that the plants were completely infected.

The active compounds, active compound concentrations and results can be seen from the following table:

Table 4

| Active compound | *Uromyces* test/protective Infection in % of the infection of the untreated control at an active compound concentration (in %) of 0.005% |
|---|---|
| 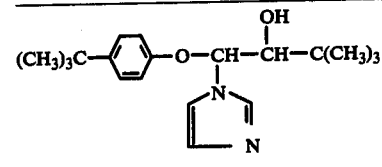 (known) (E) | 71 |
| 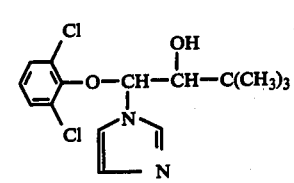 (known) (F) | 50 |
| 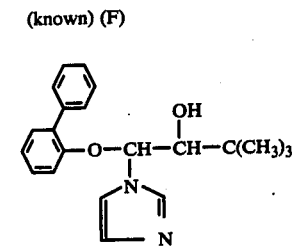 (known) (G) | 56 |
| 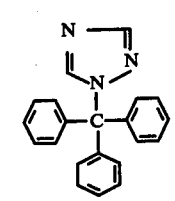 (known) (A) | 62 |

Table 4-continued

| Active compound | *Uromyces* test/protective Infection in % of the infection of the untreated control at an active compound concentration (in %) of 0.005% |
|---|---|
| (2) | 34 |
| (4) | 0 |
| (10) | 2 |
| (9) | 0 |

EXAMPLE 5

*Mycelium* growth test

Nutrient medium used:
  20 parts by weight of agar-agar
  200 parts by weight of potato decoction
  5 parts by weight of malt
  15 parts by weight of dextrose
  5 parts by weight of peptone
  2 parts by weight of disodium hydrogen phosphate
  0.3 part by weight of calcium nitrate
Composition of the solvent mixture
  0.19 part by weight of dimethylformamide or acetone
  0.01 part by weight of emulsifier (alkylaryl polyglycol ether)
  1.80 parts by weight of water
  2 parts by weight of solvent mixture
Ratio of solvent mixture to nutrient medium:
  2 parts by weight of solvent mixture
  100 parts by weight of agar nutrient medium The amounts of active compound required for the desired active compound concentration in the nutrient medium was mixed with the stated amount of solvent mixture. The concentrate was thoroughly mixed, in the stated proportion, with the liquid nutrient medium (which had been cooled to 42° C.) and was then poured into Petri dishes of 9 cm diameter. Control plates to which the preparation had not been added were also set up.

When the nutrient medium had cooled and solidified, the plates were inoculated with the species of fungi stated in the table and incubated at about 21° C.

Evaluation was carried out after 4–10 days, dependent upon the speed of growth of the fungi. When evaluation was carried out the radial growth of the mycelium on the treated nutrient media was compared with the growth on the control nutrient medium. In the evaluation of the fungus growth, the following characteristic values were used:

| | |
|---|---|
| 1 | no fungus growth |
| up to 3 | very strong inhibition of growth |
| up to 5 | medium inhibition of growth |
| up to 7 | slight inhibition of growth |
| 9 | growth equal to that of untreated control. |

The active compounds, the active compound concentrations and the results can be seen from the following table:

Table 5

Mycelium growth test

| Active compounds | Active compound concentration = 10 ppm | Fusarium culmorum | Sclerotinia sclerotiorum | Fusarium nivale | Colletotrichum coffeanum | Rhizoctonia solani | Pythium ultimum | Cochliobolus miyabeanus | Botrytis cinerea | Verticillium alboatrum | Pyricularia oryzae | Phialophora cinerescens | Helminthosporium gramineum | Mycosphaerella musicola | Phytophthora cactorum | Pellicularia sasakii |
|---|---|---|---|---|---|---|---|---|---|---|---|---|---|---|---|---|
| (known) A | | 9 | 9 | 9 | 9 | 9 | 9 | 9 | 9 | 9 | 9 | 9 | 9 | 9 | 9 | 9 |
| (known) (H) | | 9 | 9 | 9 | 9 | 9 | 9 | 9 | 5 | 9 | 9 | 9 | 5 | 9 | 5 | 9 |
| (known) (E) | | 9 | 9 | 9 | 9 | 9 | 9 | 9 | 9 | 9 | 9 | 5 | 9 | 9 | 9 | 9 |
| (2) | | 5 | 3 | 5 | 5 | 5 | 3 | — | 5 | 5 | 1 | 3 | 2 | 1 | 5 | 5 |

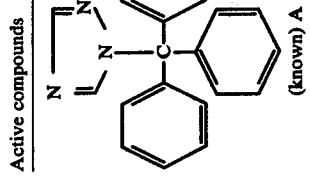

(known) A

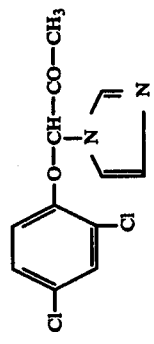

(known) (H)

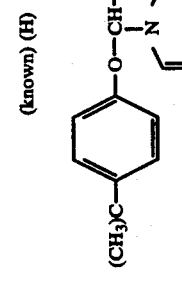

(known) (E)

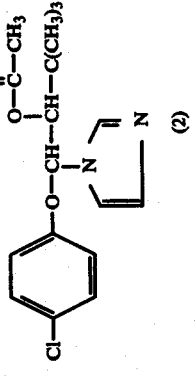

(2)

Table 5-continued

| Active compounds | Active compound concentration = 10 ppm | Mycelium growth test | | | | | | | | | | | | | |
|---|---|---|---|---|---|---|---|---|---|---|---|---|---|---|---|
| | | Fungi | | | | | | | | | | | | | |
| | | Fusarium culmorum | Sclerotinia sclerotiorum | Fusarium nivale | Colletotrichum coffeanum | Rhizoctonia solani | Pythium ultimum | Cochliobolus miyabeanus | Botrytis cinerea | Verticillium alboatrum | Pyricularia oryzae | Phialophora cinerescens | Helminthosporium gramineum | Mycosphaerella musicola | Phytophthora cactorum | Pellicularia sasakii |
| (4) biphenyl with O-CH(C(CH₃)₃)-O-C(=O)-CH₃ and pyrazolyl | | 3 | 3 | 5 | 1 | 5 | 5 | 3 | 3 | 5 | 1 | 3 | 1 | 1 | 5 | 1 |
| (10) 2-chloro-4-phenylphenyl with O-CH(C(CH₃)₃)-O-C(=O)-CH₃ and pyrazolyl | | — | 5 | — | — | 3 | 5 | 5 | 5 | 5 | 1 | 3 | — | — | 3 | 5 |
| (9) 4'-chloro-4-biphenyl with O-CH(C(CH₃)₃)-O-C(=O)-CH₃ and pyrazolyl | | 5 | 5 | 5 | — | 1 | 3 | 3 | 5 | — | 1 | — | 1 | — | 5 | 1 |
| (8) 2-cyclohexylphenyl with O-CH(C(CH₃)₃)-O-C(=O)-CH₃ and pyrazolyl | | — | 3 | 5 | — | 5 | — | 5 | 3 | — | 5 | — | — | — | 1 | 5 |

Table 5-continued

| Active compounds | Active compound concentration = 10 ppm | Mycelium growth test | | | | | | | Fungi | | | | | | | |
|---|---|---|---|---|---|---|---|---|---|---|---|---|---|---|---|---|
| | | Fusarium culmorum | Sclerotinia sclerotiorum | Fusarium nivale | Colletotrichum coffeanum | Rhizoctonia solani | Pythium ultimum | Cochliobolus miyabeanus | Botrytis cinerea | Verticillium alboatrum | Pyricularia oryzae | Phialophora cinerescens | Helminthosporium gramineum | Mycosphaerella musicola | Phytophthora cactorum | Pellicularia sasakii |
| X 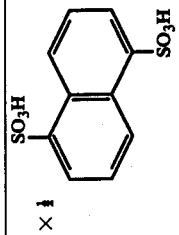 | | | | | | | | | | | | | | | | |

The following further examples are set forth to illustrate, without limitation, the manner of producing the instant compounds according to the present invention.

EXAMPLE 6

(a) Starting material

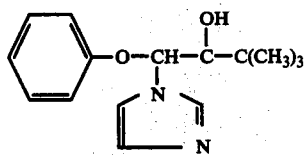

25.8 g (0.1 mole) of 1-imidazolyl-(1)-1-phenoxy-3,3-dimethyl-butan-2-one were dissolved in 250 ml of methanol and 5.9 g (0.15 mole) of sodium borohydride were introduced, in portions, into this solution while stirring and using reflux cooling at 5 to 10° C. After stirring for 15 hours at room temperature, 20 ml of concentrated hydrochloric acid were added and the reaction mixture was stirred for a further 15 hours at room temperature, and poured into 300 ml of saturated sodium bicarbonate solution. It was extracted twice with 100 ml of methylene chloride at a time, the organic phase was washed twice with 100 ml of water at a time and dried over sodium sulfate, and the solvent was distilled off in a waterpump vacuum. The residue was triturated with 30 ml of petroleum ether. 21.6 g (83% of theory) of 1-imidazolyl-(1)-1-phenoxy-3,3-dimethyl-butan-2-ol were obtained as an isomer mixture of melting point 99–105° C.

(b)

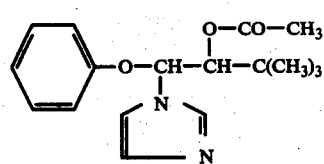

(Process variant (a))

8.0 g (0.1 mole) of acetyl chloride were added at room temperature to 20.6 g (0.1mole) of 1-imidazolyl-(1)-1-phenoxy-3,3-dimethyl-butan-2-ol in 100 ml of ethyl acetate. The mixture was then heated for 4 hours under reflux, and was allowed to cool and was concentrated by distilling off the solvent in vacuo. The residue was taken up in benzene and the solution was washed with aqueous sodium bicarbonate solution and dried over sodium sulfate. The solvent was distilled off in a waterpump vacuum and the residue was recrystalli ed from petroleum ether. 20.6g (45% of theory) of 2-acetoxy-1-phenoxy-1-imidazolyl-(1)-3,3-dimethyl-butane were obtained as an isomer mixture of melting point 114–121° C.

EXAMPLE 7

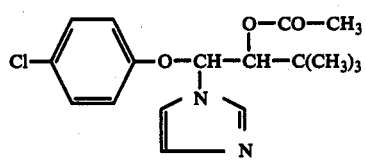

(Process variant (b))

8.0 g (0.027 mole) of 1-(4-chlorophenoxy)-1-imidazolyl-(1)-3,3-dimethyl-butan-2-ol in 40 ml of acetic anhydride were heated with 0.15 g of sodium acetate for 10 hours at 100° C. The solution was then cooled and stirred into 400 ml of ice water, the temperature being kept at 20–25° C. The mixture was left to stand overnight. A smeary, crystalline mass precipitated, which was taken up in chloroform. The solution was washed repeatedly with water and sodium bicarbonate solution, dried over sodium sulfate and concentrated in vacuo by distilling off the solvent. The crystalline residue was boiled in petroleum ether, filtered off cold and dried. 4.5 g (49% of theory) of 2-acetoxy-1-(4-chlorophenoxy)-1-imidazolyl-(1)-3,3-dimethyl-butane were obtained as an isomer mixture of melting point 81–91° C.

The following examples of the general formula were obtained analogously to the above examples:

Table 6

| Compound No. | $X_n$ | R | Melting point(° C) as the isomer mixture |
|---|---|---|---|
| 3 | 4-F | $CH_3$ | 144–153 |
| 4 | 4-(phenyl) | $CH_3$ | 117–124 |
| 5 | 4-Br | $CH_3$ | 78–89 |
| 6 | 4-(cyclohexyl) | $CH_3$ | 254–257 (× ½) (naphthalene-1,5-disulfonic acid) |

Table 6-continued $$\text{(I)} \quad \underset{X_n}{\text{Ph}}-\overset{\text{O-CO-R}}{\underset{\underset{\text{N}\diagdown\diagup\text{N}}{|}}{\text{O-CH-CH-C(CH}_3)_3}}$$

| Compound No. | $X_n$ | R | Melting point (°C) as the isomer mixture |
|---|---|---|---|
| 7 | 2-phenyl | CH₃ | 161–174 (× ½ naphthalene-1,5-disulfonic acid) |
| 8 | 2-cyclohexyl | CH₃ | 250–256 decomposition (× ½ naphthalene-1,5-disulfonic acid) |
| 9 | 4-Cl-phenyl | CH₃ | 118–129 |
| 10 | 2-Cl,4-phenyl | CH₃ | 92–97 |
| 11 | 3-Br | CH₃ | 260–262 (× ½ naphthalene-1,5-disulfonic acid) |
| 12 | 2,6-Cl₂,4-phenyl | CH₃ | 246–251 (× ½ naphthalene-1,5-disulfonic acid) |
| 13 | 4-I | CH₃ | 100–106 |
| 14 | 2-F | CH₃ | 91–102 |
| 15 | 4-Cl | CH₂Cl | 194 (× HCl) |
| 16 | 4-Cl | CHCl₂ | 205–207 (× HCl) |
| 17 | 4-Cl | —CH₂—CH(CH₃)₂ | 232–236 (× ½ naphthalene-1,5-disulfonic acid) |
| 18 | 4-Cl | —(CH₂)₁₆CH₃ | 128–141 (× ½ naphthalene-1,5-disulfonic acid) |

Table 6-continued $$\underset{X_n}{\text{[phenyl]}}\text{O—CH—CH—C(CH}_3)_3 \quad (I)$$
with O—CO—R on CH, and N-linked imidazole

| Compound No. | $X_n$ | R | Melting point(° C) as the isomer mixture |
|---|---|---|---|
| 19 | 4-Cl | —NH—C(CH$_3$)$_3$ | 111–115 |
| 20 | 4-Cl | —NH—CH$_3$ | 183–190 |
| 21 | 4-Cl | —NH—[phenyl] | 170–173 |
| 22 | 4-Cl | —NH—[phenyl]—Cl | 177–185 |
| 23 | 2-Cl, 4-Cl [phenyl] | CH$_3$ | 219–221 (× HCl) |

Other compounds which can be similarly prepared include:

TABLE 7

| $X_n$ | R |
|---|---|
| 4-NH$_2$ | —CH$_2$—CH$_2$—CH$_3$ |
| 4-CN | —CH$_2$—C≡CH |
| 4-NO$_2$ | [cyclohexyl] |
| 4-C$_4$H$_9$-n | —[phenyl] |
| 4-OC$_2$H$_5$ | —CH$_2$—O—[phenyl] |
| 3-CF$_3$ | —[phenyl]—Cl |
| 4-SC$_2$H$_5$ | —C$_2$H$_4$—O—[phenyl]—NH$_2$ |
| 4-C(O)OC$_2$H$_5$ | —[phenyl]—NH$_2$ |
| 4-O—[phenyl] | —[phenyl]—CN |

TABLE 7-continued

| $X_n$ | R |
|---|---|
| 4-[phenyl]-NH$_2$ | —CH$_2$—[phenyl]—NH$_2$ |
| 4-O—[phenyl] | —[phenyl]—C$_2$H$_5$ |
| 4-[phenyl]—NO$_2$ | —N(C$_3$H$_7$-i)$_2$ |
| 4-O—[phenyl] | —NH—[phenyl] |
| 4—CH$_2$—[phenyl] | —NH—[phenyl] |
| 4—C$_2$H$_4$—[phenyl] | —CH$_3$ |
| 4—CH$_2$—[phenyl] | —CH$_3$ |
| 4—C$_2$H$_4$—[phenyl] | —CH$_3$ |

TABLE 7-continued

| $X_n$ | R |
|---|---|
| 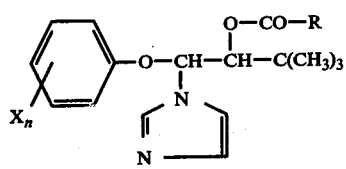 | —CH$_3$ | and the like.

It will be appreciated that the instant specification and examples are set forth by way of illustration and not limitation, and that various modifications and changes may be made without departing from the spirit and scope of the present invention.

What is claimed is:

1. A 2-acyloxy-1-phenoxy-1-imidazolyl-(1)-3,3-dimethyl-butane of the formula

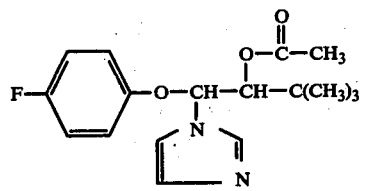

in which
R is alkyl with 1 to 8 carbon atoms, alkenyl or alkynyl with 2 to 4 carbon atoms, cycloalkyl with 5 to 7 carbon atoms, haloalkyl with 1 or 2 carbon atoms and 1 to 5 halogen atoms; phenyl or phenoxyalkyl (the alkyl moiety having 1 or 2 carbon atoms), the phenyl or phenoxy being optionally substituted by halogen, amino, cyano, nitro or alkyl with 1 or 2 carbon atoms; alkylamino or dialkylamino with 1 to 4 carbon atoms in each alkyl; or phenylamino optionally substituted by halogen, nitro or cyano;
X is halogen, amino, cyano, nitro, alkyl with 1 to 4 carbon atoms, cycloalkyl with 5 to 7 carbon atoms, alkoxy with 1 or 2 carbon atoms, haloalkyl with 1 or 2 carbon atoms and 1 to 5 halogen atoms, alkylthio with 1 or 2 carbon atoms, or alkoxycarbonyl with a total of up to 5 carbon atoms; phenyl or phenoxy optionally substituted by halogen, amino, cyano, nitro or alkyl with 1 or 2 carbon atoms; or phenylalkyl (having 1 or 2 carbon atoms in the alkyl moiety) optionally substituted in the phenyl by halogen, nitro or cyano and optionally substituted in the alkyl by alkylcarbonyloxy with a total of up to 3 carbon atoms; and
n is 0 or an integer from 1 to 5,
or a salt thereof with a physiologically tolerated acid.

2. A compound according to claim 1 in which n is 0, 1, 2 or 3.

3. The compound according to claim 1 wherein such compound is 2-acetoxy-1-(4-chlorophenoxy)-1-imidazolyl-(1)-3,3-dimethyl-butane of the formula

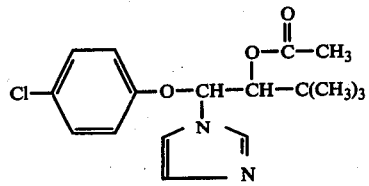

or a salt thereof with a physiologically tolerated acid.

4. The compound according to claim 1 wherein such compound is 2-acetoxy-1-(4-fluorophenoxy)-1-imidazolyl-(1)-3,3-dimethyl butane of the formula

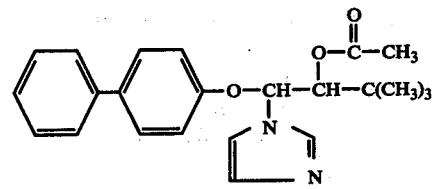

or a salt thereof with a physiologically tolerated acid.

5. The compound according to claim 1 wherein such compound is 2-acetoxy-1-(4-diphenyloxy)-1-imidazolyl-(1)-3,3-dimethylbutane of the formula

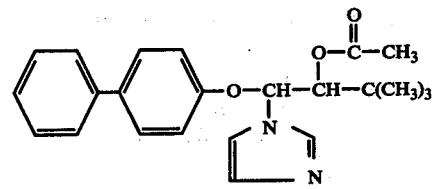

or a salt thereof with a physiologically tolerated acid.

6. The compound according to claim 1 wherein such compound is 2-acetoxy-1-(4-bromophenoxy)-1-imidazolyl-(1)-3,3-dimethyl butane of the formula

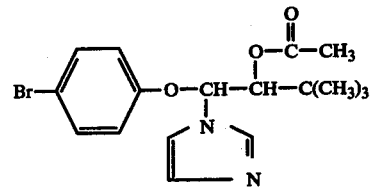

or a salt thereof with a physiologically tolerated acid.

7. The compound according to claim 1 wherein such compound is 2-acetoxy-1-[4-(4'-chlorophenyl)-phenoxy]-1-imidazolyl-(1)-3,3-dimethyl butane of the formula

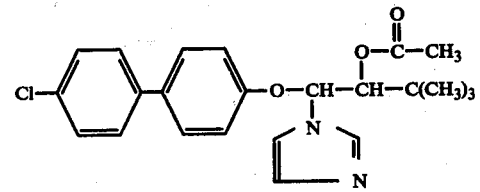

or a salt thereof with a physiologically tolerated acid.

8. The compound according to claim 1 wherein such compound is 2-acetoxy-1-(2-chloro-4-phenyl-phenoxy)-1-imidazolyl-(1)-3,3-dimethyl-butane of the formula

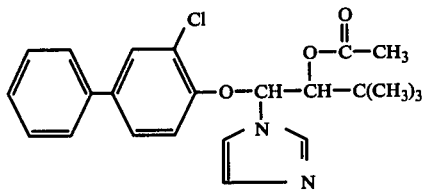

or a salt thereof with a physiologically tolerated acid.

9. A method of combating plant fungus or bacteria pests which comprises applying to plants, seed or soil a fungicidally or bactericidally effective amount of a compound according to claim 1.

10. The method according to claim 9 in which said compound is 2-acetoxy-1-(4-chlorophenoxy)-1imidazolyl-(1)-3,3-dimethyl-butane, 2-acetoxy-1-(4-fluorophenoxy)-1-imidazolyl-(1)-3,3-dimethyl-butane, 2-acetoxy-1-(4-diphenyloxy)-1-imidazolyl-(1)-3,3-dimethyl-butane, 2-acetoxy-1-(4-bromophenoxy)-1-imidazolyl-(1)-3,3-dimethyl-butane, 2-acetoxy-1-[4-(4'-chlorophenyl)-phenoxy]-1-imidazolyl-(1)-3,3-dimethyl-butane, or 2-acetoxy-1-(2-chloro-4-phenyl-phenoxy)-1-imidazolyl-(1)-3,3-dimethyl-butane, or a salt thereof with a physiologically tolerated acid.